United States Patent
Liu et al.

(10) Patent No.: US 6,447,490 B1
(45) Date of Patent: *Sep. 10, 2002

(54) VAGINA CLEANING SYSTEM FOR PREVENTING PREGNANCY AND SEXUALLY TRANSMITTED DISEASES

(76) Inventors: James Zhou Liu, 462 Burns Dr., Westerville, OH (US) 43082; Shen Pan, 462 Burns Dr., Westerville, OH (US) 43082

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/573,014

(22) Filed: May 17, 2000

Related U.S. Application Data

(63) Continuation-in-part of application No. 09/201,219, filed on Nov. 30, 1998, which is a continuation-in-part of application No. 08/908,419, filed on Aug. 7, 1997, now abandoned.

(51) Int. Cl.$^7$ ............................................. A61M 31/00
(52) U.S. Cl. .................. 604/279; 604/36; 604/515; 604/257; 604/275; 600/220; 600/210
(58) Field of Search .............................. 604/39, 43, 48, 604/500, 514, 515, 517, 36, 275, 19, 181, 187.2, 212, 213, 216, 217, 104, 262, 408, 75, 279, 257; 606/119; 600/184, 192, 220, 210

(56) References Cited

U.S. PATENT DOCUMENTS

| | | | |
|---|---|---|---|
| 258,140 A | | 5/1882 | Sims |
| 471,647 A | | 3/1892 | Magoris |
| 693,358 A | | 2/1902 | Westlake |
| 735,276 A | | 8/1903 | Lane |
| 1,080,395 A | | 12/1913 | Wilde |
| 1,535,756 A | | 4/1925 | Austin |
| 1,665,564 A | | 4/1928 | Reitz |
| RE17,319 E | | 6/1929 | Parkler |
| 1,823,951 A | | 9/1931 | O'Neill |
| 2,792,003 A | | 5/1957 | Cantor ........................ 128/235 |
| 2,881,760 A | * | 4/1959 | McGiveran et al. ........ 604/213 |
| 3,010,454 A | | 11/1961 | Lucie et al. ................. 128/251 |
| 3,037,505 A | * | 6/1962 | Walden et al. .............. 604/109 |
| 3,127,893 A | | 4/1964 | Montague .................... 128/239 |
| 3,144,866 A | | 8/1964 | Ellis ........................... 128/232 |
| 3,154,074 A | | 10/1964 | Harrison ..................... 128/232 |
| 3,154,076 A | | 10/1964 | O'Donnell .................. 128/260 |
| 3,421,509 A | | 1/1969 | Fiore .......................... 128/349 |
| 3,622,049 A | * | 11/1971 | Thompson .................. 222/190 |
| 3,771,522 A | | 11/1973 | Waysilk et al. ............. 128/227 |
| 3,894,539 A | | 7/1975 | Tallent ........................ 128/261 |

(List continued on next page.)

Primary Examiner—Glenn K. Dawson
Assistant Examiner—Jennifer Maynard
(74) Attorney, Agent, or Firm—Standley & Gilcrest LLP

(57) ABSTRACT

The present invention discloses an improved vagina cleaning system. The improved system comprises a vagina opener, a vagina cleaning-solution sprayer, a multiple-functional vagina cleaning solution, and a health-promoting bacteria introducer. The system is used to remove semen from the vagina to prevent pregnancy, to reduce pathogenic microorganisms in the vagina to prevent sexually transmitted diseases, to remove other unwanted materials from the vagina to eliminate discomfort, and to add health-promoting bacteria into the vagina to prevent abnormal colonization of microflora in the vaginal cavity. The present invention also discloses methods of using the system for cleaning the vaginal cavity and for introducing health-promoting bacteria into the vaginal cavity.

19 Claims, 3 Drawing Sheets

A Vagina Cleaning Sprayer Bottle

U.S. PATENT DOCUMENTS

| | | | |
|---|---|---|---|
| 4,066,080 A | | 1/1978 | Sneider .................. 128/251 |
| 4,068,663 A | | 1/1978 | D'Alessandro ............ 128/232 |
| 4,309,995 A | | 1/1982 | Sacco .................... 128/239 |
| 4,321,920 A | | 3/1982 | Gillig ................... 128/239 |
| 4,592,748 A | * | 6/1986 | Jost ..................... 604/279 |
| 4,601,709 A | | 7/1986 | Kabbaby .................. 604/150 |
| 4,842,583 A | | 6/1989 | Majlessi ................. 604/43 |
| 4,894,053 A | | 1/1990 | Reddick .................. 604/85 |
| 4,950,231 A | * | 8/1990 | Liu ...................... 604/39 |
| 5,179,938 A | * | 1/1993 | Lonky .................... 128/18 |
| 5,241,714 A | | 9/1993 | Barry .................... 4/605 |
| 5,304,116 A | | 4/1994 | Cornelius ................ 604/39 |
| 5,377,667 A | * | 1/1995 | Patton et al. ............ 128/3 |
| 5,423,764 A | | 6/1995 | Fry ...................... 604/187 |
| 5,447,496 A | | 9/1995 | Bove et al. .............. 604/54 |
| 5,573,765 A | * | 11/1996 | Reinhard et al. .......... 424/93.45 |
| 5,827,543 A | * | 10/1998 | Fitzgerald ............... 424/653 |
| 5,946,741 A | | 9/1999 | Moon ..................... 4/420.1 |

* cited by examiner

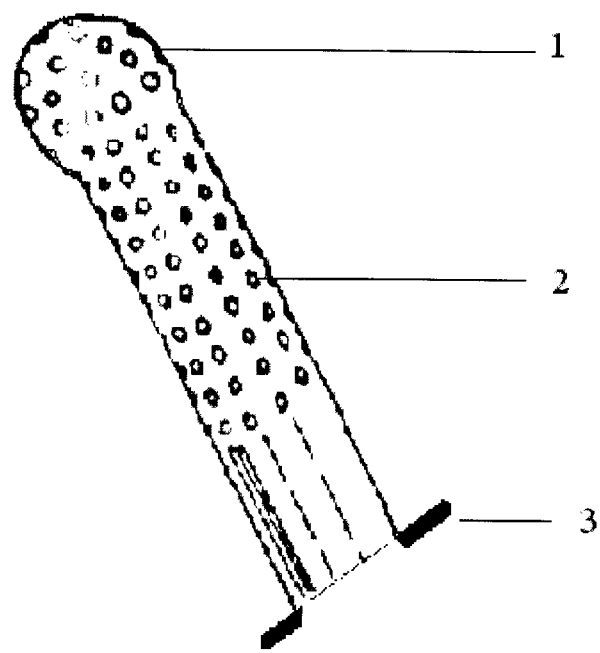
Figure 1. A Penis-Shaped Vagina Opener
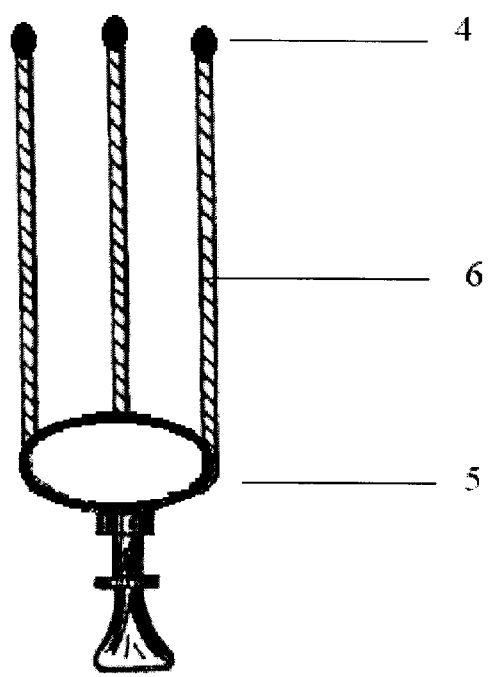
Figure 2. A Three-Leg Shaped Vagina Opener

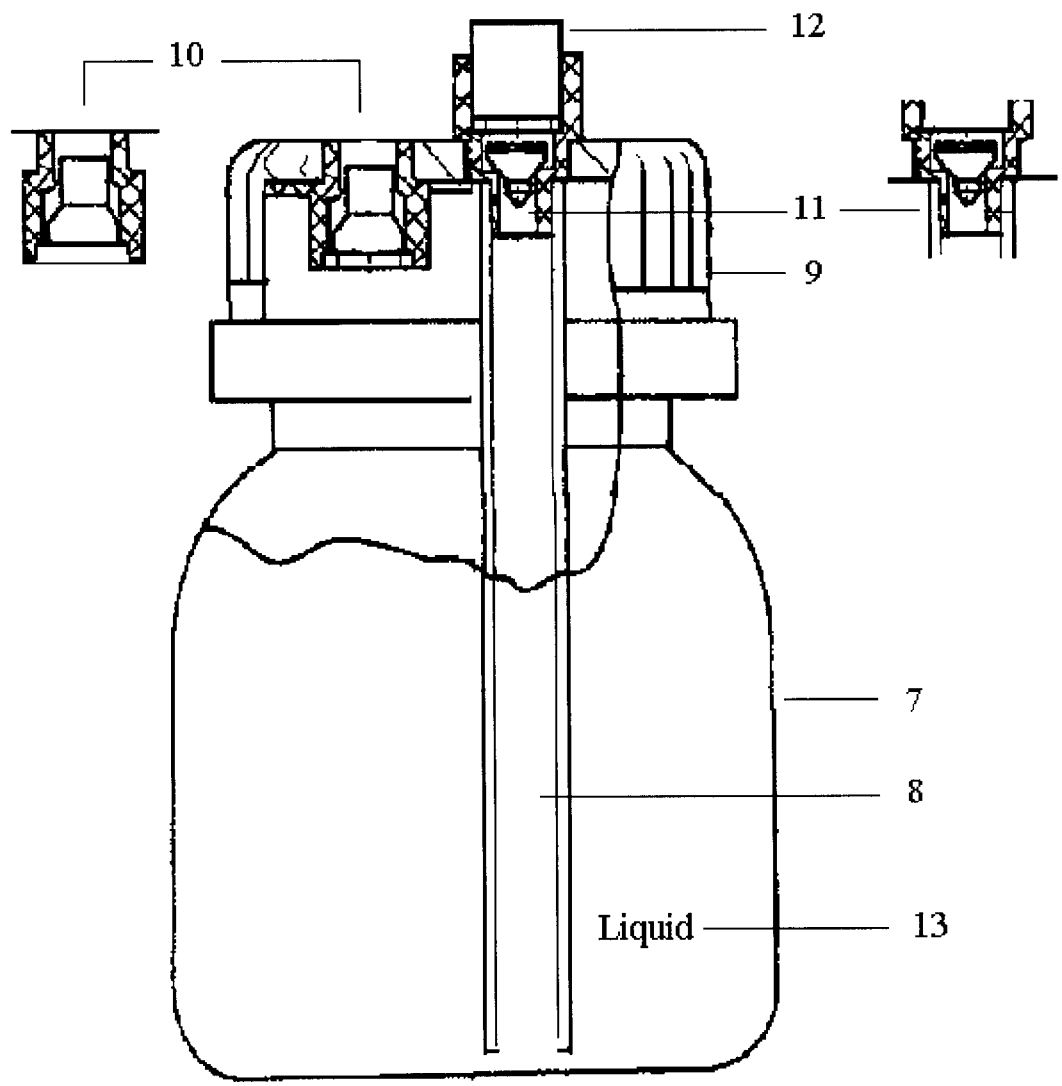
Figure 3. A Vagina Cleaning Sprayer Bottle

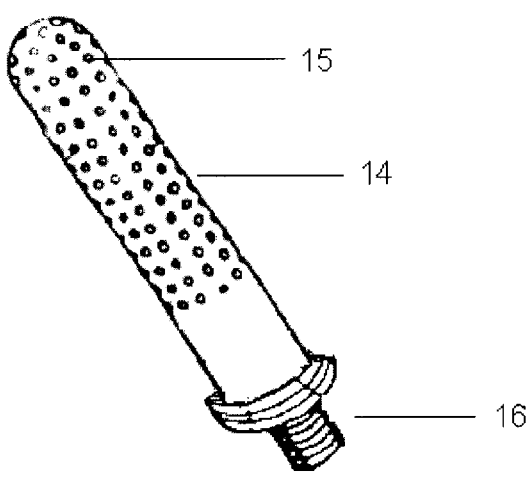
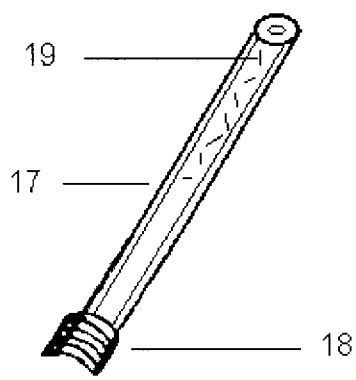
Figure 4. A Sprayer Head
Figure 5. A Health-Promoting Bacteria Introducer

VAGINA CLEANING SYSTEM FOR PREVENTING PREGNANCY AND SEXUALLY TRANSMITTED DISEASES

RELATED APPLICATIONS

This is a continuation-in-part of application Ser. No. 09/201,219, filed Nov. 30, 1998, now pending, which itself is a continuation-in-part of application Ser. No. 08/908,419, filed Aug. 7, 1997, now abandoned.

BACKGROUND OF THE INVENTION

1. Field of the Invention

The present invention relates generally to an improved vagina cleaning system to be used for removing unwanted substances from a woman's vagina. The vagina cleaning system of the present invention includes an improved vagina opener, a simplified vagina-cleaning device and a multi-functional vagina cleaning solution. A device used to introduce health-promoting probiotic bacteria into the vagina may also be used as part of the system. Also included is a method of using the vagina cleaning system of the present invention.

2. Description of the Related Arts

The incidence of sexually transmitted diseases, including human immunodeficiency virus (HIV) infection, is increasing in children, adolescents, young adults, as well as others who are sexually active. It has been reported that approximately 50% of American adolescents are sexually active by age 16 years (Committee on Infectious Diseases, American Academy of Pediatrics: 1994 Red Book, Report of the Committee on Infectious Diseases, 23rd edition, G. Peter, N. A. Halsey, E. K. Marcuse & L. K. Pickering, eds. p. 103, American Academy of Pediatrics, 1994, Elk Grove Village, Ill.). Sexually experienced adolescents have the highest rate of sexually transmitted diseases as compared to any age group. Being pregnant is not the desired consequence of sexual activity for most adolescent girls.

The American Academy of Pediatrics reported that traditional sexually transmitted diseases, including syphilis, gonorrhea, chancroid, and lymphogranuloma venereum, are still prevalent today. Currently, HIV, hepatitis B virus and Chlamydia trachomatis are major pathogens of sexually transmitted diseases (Committee on Infectious Diseases, American Academy of Pediatrics: 1994 Red Book. Report of the Committee on Infectious Diseases, 23rd edition, G. Peter, N. A. Halsey, E. K. Marcuse & L. K. Pickering, eds. pp. 104–106, American Academy of Pediatrics, 1994, Elk Grove Village, Ill.). Although certain sexually transmitted diseases are treatable, some of those caused by Candida albicans, cytomegalovirus, HIV, and Herpes simplex types 1 and 2, lack effective and/or inexpensive treatment methods.

Major results of sexually transmitted diseases in child-bearing women include HIV infection, chronic hepatitis, salpingitis, ectopic pregnancies, and infertility. Carcinoma of the cervix is also related to sexually transmitted diseases (X. Castellsague et al., Prevalence of Penile Human Papillomavirus DNA in Husbands of Women with and Without Cervical Neoplasis: a Study in Spain and Colombia, *The Journal of Infectious Diseases*, 176, pp. 353–361, 1997). Furthermore, sexually transmitted diseases cause neonatal infections, such as HIV, hepatitis B virus, and Herpes simplex (R. C. Hershow et al., Increased Vertical Transmission of Human Immunodeficiency Virus from Hepatitis C Virus Co-Infected Mothers, The Journal of Infectious Diseases, 176, pp. 414–420, 1997). Sexually transmitted diseases also cause premature delivery, a significant problem in the neonatal care area (Committee on Infectious Diseases, American Academy of Pediatrics, 1994 Red Book: Report of the Committee on Infectious Diseases, 23rd edition, G. Peter, N. A. Halsey, E. K. Marcuse & L. K. Pickering, eds. pp. 104–106, American Academy of Pediatrics, 1994, Elk Grove Village, Ill.). Urinary tract infections among females are often acute and recurring. Sex partners have been identified to be the pathogen carriers (B. Foxman et al., Transmission of Uropathogens Between Sex Partners, The Journal of Infectious Diseases, 173, pp. 989–992, 1997).

Worldwide sexually transmitted diseases cause serious health problems. Those diseases not only decrease the quality of a patients' life, but also lead to harmful effects for the next generation. Therefore, a simple and effective method for preventing sexually transmitted diseases is needed.

Condom use has been recognized as the most effective method in preventing many kinds of sexually transmitted diseases. However, condom use has many problems. First, for many people using a condom results in reduced sensation or decreased sexual pleasure. Second, the condom may break or slip off during intercourse (M. Steiner et al., Can Condom Users Likely to Experience Condom Failure be Identified? *Fam-Plann-Perspect.*, 25(5), pp. 620–223 & 226,1993). Third, using a condom sends unwanted messages to one's partner that the user might have a sexually transmitted disease, especially HIV infection. Fourth, frequently buying condoms is an embarrassment for the frequent condom user (W. R. Grady et al., Condom Characteristics: The Perceptions and Preferences of Men in the United States, *Fam-Plann-Perspect.*, 25(2), pp. 67–73, 1993). Thus, there is a need for a new method of preventing sexually transmitted diseases.

Men, to clean their penises for preventing sexually transmitted diseases, have used soap and water (N. O'Farrell, Soap and Water Prophylaxis for Limiting Genital Ulcer Diseases and HIV-1 Infection in Men in Sub-Saharan Africa, *Genitourin-Med*, 69(4), pp. 297–300, 1993). However, this method is not as easy for women to clean the vaginal cavity due to practical reasons.

Many methods can be used to prevent pregnancy. The use of a condom is one of the most common and effective methods to prevent unwanted pregnancy. However, due to many reasons, as stated in the above paragraphs, people do not want to use a condom. For adolescents, the rate of condom use is lower than adults, due to many known and unknown reasons. Since teenage pregnancy is one of the most unwanted consequences of the sexual activity, it is necessary to have some alternative methods to prevent unwanted pregnancy. The significant removal of semen from the vagina can largely reduce the chance of pregnancy.

Several instruments have been invented for washing the vagina. William Sims introduced a vagina washing system that included water as a washing solution, a washing device and a vagina opener with a solid wall (U.S. Pat. No. 258,140, May 16, 1882). The use of this system cannot effectively clean the vaginal cavity due to the fact that the vagina opener creates a dead space between the outside wall of the opener and the vaginal cavity, in which the washing solution cannot reach. The second problem associated with the Sims' vaginal washing system is that it is very inconvenient to carry this system when the user is traveling. Also, a more efficient vagina washing solution, rather than just water, is needed. Therefore, there is a need to improve the Sims system. Anthony E. Magoris invented a spectrum-like tool for cleaning the vagina (U.S. Pat. No. 471,647, Mar. 29, 1892). Edward B. Cantor (U.S. Pat. No. 2,792,003, May 4, 1957), John R. Lane (U.S. Pat. No. 735,276, Aug. 4, 1903), and Arthur E. Wilde (U.S. Pat. No. 1,080,395, Feb. 19, 1913), all invented a syringe-like tool for cleaning the vagina. All of the above devices have the same problem in that a dead space is created between the wall of the vagina opener and the vaginal cavity, and the washing solution cannot reach that dead space. Henricus W. Westlake created a vaginal irrigator (U.S. Pat. No. 693,358, Feb. 11, 1902). Four disadvantages exist in Westlake's system: (1) it is relatively difficult to manufacture Westlakes' device; (2) the device is not easy to use by the individual; (3) it is expensive to purchase the whole device; and (4) the system creates a dead space between the outside wall of the device and the vaginal cavity. Lucie et al. designed a fluid dispensing device for introducing therapeutical liquid into the vagina (U.S. Pat. No. 3,010,454, Nov. 28, 1961). Ellis presented a disposable douche syringe for feminine hygiene (U.S. Pat. No. 3,144,866, Aug. 18, 1964). Like the other tools mentioned above, Lucies' and Ellis' devices could not create a space between the surface of the vaginal cavity and the outside wall of the devices. All of the introduced liquid would flow out of the vagina under pressure. The lower part of the vaginal cavity would most likely be washed, but the whole vaginal cavity would not be effectively cleaned.

Furthermore, all the currently taught vaginal cleaning devices and douche bags not only reduce/eliminate pathogenic substances in the vagina, but also eliminate the health-promoting bacteria, such as lactobacilli. Without a normal microflora in the vagina, many other problems may occur, such as the increased risk of allergic reactions. The present invention provides an improved system to efficiency clean the vagina and to help to maintain the normal microflora of the vagina.

SUMMARY OF THE INVENTION

The present invention is a method to meet women's needs by providing a simple, cheap, highly effective and easily operable tool to remove semen from the vaginal cavity that may result in the prevention of pregnancy. The present invention is to a method to remove/reduce the existence of newly introduced infectious agent(s) in the vagina, which may result in preventing sexually transmitted diseases. The present invention is to a method to shorten the duration of the waste metabolites staying in the vagina that may result in decreasing discomfort. And, additionally, the present invention is to a method to maintain a healthy microflora in the vagina.

The present invention discloses a vagina cleaning system. The vagina cleaning system comprises an opener for increasing vagina cleaning efficiency, an easily operable cleaning-solution injector, a multi-functional vagina cleaning solution, and a device for adding health-promoting probiotic bacteria into the vagina.

BRIEF DESCRIPTION OF THE DRAWINGS

FIG. 1 shows a penis-shaped vagina opener, according to one embodiment of the present invention.

FIG. 2 shows a three-legged shaped vagina opener, according to one embodiment of the present invention.

FIG. 3 shows a cleaning solution sprayer, according to one embodiment of the present invention.

FIG. 4 shows a multi-hole cleaning solution sprayer head, according to one embodiment of the present invention.

FIG. 5 shows a health-promoting bacteria introducer, according to one embodiment of the present invention.

DETAILED DESCRIPTION OF THE INVENTION

FIG. 1 is a penis-shaped vagina opener. This is a disposable and/or reusable device and is easy to insert into the vagina and easy to keep in the vagina without the aid of the user's hands. The nozzle is a hollow-tube which creates an open space in the vaginal cavity. This opener has an oval outer head 1, and the other end is an extended tube with a handle 3. On the body and head of the nozzle there are many small holes, 2, used to maximize the surface area the cleaning solution is able to contact in the vaginal cavity. When the vagina opener has been inserted into the vagina, it provides a hollow space in the center for the user to put the vagina cleaning solution injector, which will be described in detail below. The size of the penis-shaped vagina opener is as follows: the length of the vagina opener is between 3 and 15 centimeters, and preferably about 8 centimeters. The external diameter of the vagina opener is from 0.5 to 4.0 centimeters. Preferably, the diameter is from 1.0 to 2.0 centimeters. The diameter of the holes 2 on the wall of the vagina opener is about 0.1 to 0.3 centimeters. Preferably, their diameter is about 0.2 centimeters.

FIG. 2 is a three-legged shaped vagina opener in the open position. Its closed position is not shown. The three legs, 6, are connected to an open-close regulator 5. The close position is used at the time of insertion and the open position is used at the time of cleaning. The three legs 6 are the same in size and in shape, and are in a 60° angle from one another in the open position. One end of the leg 4, which will be first inserted into the vagina, is shaped like a ball. This is to achieve the maximum degree of smoothness during insertion and removal from the vagina. The other end of each of the three legs is screwed tightly and connected to the open-close regulator 5. The open-close regulator 5 may be made in any way that is taught in prior art.

Any materials safe for contacting the vaginal cavity will be suitable for manufacturing the vaginal openers, such as plastic, stainless metals, rubber or other suitable materials. These materials may be used singularly, or in combination. The external and internal surfaces of the vagina opener must be very smooth. The outer-end of the vagina opener may be marked in an up/down direction to easily recognize the correct position. The whole vagina opener may be marked with a centimeter graduation starting from either end. The scale may also be marked in inches and parts thereof. Under normal conditions the vagina opener is not breakable when it is inserted into the vagina and during cleaning process. The vagina opener may be re-usable, or may be disposable depending on the materials used to manufacture it, or depending on the users' need and preference. If the disposable vagina opener is used, a water-activated lubricant may be applied on the surface during the manufacturing process. If the re-usable vagina opener is made, a package of a lubricant may accompany the product when purchased.

FIG. 3 is a vagina cleaning-solution sprayer. This sprayer is used to deliver cleaning solution into the vaginal cavity. The vagina cleaning solution sprayer may compromise two parts, the sprayer bottle 7 and the sprayer head 14 (shown in FIG. 4). The sprayer bottle is to hold and pump out the cleaning solution. The sprayer bottle has a unique cap 9. There are two openings in the cap. The first opening is a one-directional airflow switch 10, which may be located at any place on the cap next to the fluid-flow switch 11. This airflow switch allows the air coming into the bottle to balance the inner pressure of the sprayer bottle when the cleaning solution is squeezed out. The balanced pressure inside of the sprayer bottle makes it possible for all of the cleaning solution to be squeezed out. The second opening is a one-directional liquid-flow switch 11. Although this switch may be located at any place on the cap, it is preferably in the center of the cap. This switch only allows the solution or the air to flow out of the bottle, but does not allow any fluid to flow back into the bottle. The liquid-flow switch 11 has two ends, one end connects to the sprayer head by a screw connector 12 and the other end connects to a tube 8, which transfers the cleaning solution into sprayer head.

The sprayer head 14 delivers cleaning solution into all parts of the vaginal cavity. It is a tube-like structure and is shown in FIG. 4. One end of the sprayer head 16 connects to the fluid-flow switch on the cap of the sprayer bottle, the other end 15 has multiple small holes to allow the cleaning solution to be sprayed into all parts of the vaginal cavity after the vagina opener is in place. The outer diameter of the tube-like sprayer head 14 is about 0.5 centimeter shorter than the inner diameter of the vagina opener. The diameter of the small holes on the sprayer head of the vagina cleaning-solution sprayer is about 0.1 to 0.4 centimeters. Preferably, its diameter is about 0.2 centimeters. The length of the sprayer head is about 3 to 12 centimeters. More preferably, its length is about 5 centimeters.

Any materials safe for contacting the vaginal cavity, such as plastic, stainless metals, rubber or others may be used to manufacture the bottle and vagina-cleaning sprayer head. These materials may be used singularly, or in any combination. The surface of the sprayer head must be smooth. The sprayer head may be marked with centimeter graduations starting from either end. The scale may also be marked in inches or subparts thereof. The sprayer head is made of non-breakable material. The sprayer head may be re-usable or may be disposable, depending on the materials used to manufacture it, and depending on the users' needs and preferences.

FIG. 5 is an introducer of health-promoting bacteria. This introducer 17 is a thin tube-like apparatus. One end 19 of the introducer has a small opening to allow the contents of the introducer to be squeezed into the vagina cavity. The other end 18 is a screw-connector. The size and shape of this connector is the same as the sprayer head 16, described above. After completion of the vaginal cleaning, the user may be ready to introduce health-promoting bacteria into the vaginal cavity. The introducer then replaces the sprayer head on the sprayer bottle. The health-promoting bacteria introducer holds preferably between 0.2 to 2.0 ml. The contents of the health-promoting bacteria introducer are a yogurt-like material. The health-promoting bacteria introducer material may be manufactured in a factory to ensure that a sufficient amount of live probiotic bacteria are present at use. The contents are in a powdered form and become wet after adding 0.5 ml of water. The contents may also be available in a ready-to-use form. If the material is in a ready-to-use form, the health-promoting bacteria introducer material should be stored in a refrigerator. The composition of the health-promoting bacteria introducer material is as follows: (per one gram dry powder): dry nonfat milk 0.2 g, cornstarch 0.3 g, inulin 0.3 g, gelatin 0.1 g, culture of *Lactobacillus acidophilus* 0.1 g (containing live *Lactobacillus acidophilus* in an effective amount, preferably of not less than $10^{10}$ colony forming units per gram). Water is to be added in the ratio of about 8 parts of water to 2 parts of the dry material.

The vagina cleaning solution 13 in the sprayer bottle 7 showing in FIG. 3 may be a water-based buffer with a pH range preferably from about 4 to 7, a saline solution which contains 0.9 g NaCl in 1 liter of water, the above liquid used as a base with the addition of liquid soap or other detergents suitable for vaginal use, a water-based buffer containing antibiotics and/or anti-inflammation agents, or a water-based buffer containing spermicides. The cleaning solution may contain all of the above mentioned active ingredients to have a multiple cleaning function. The temperature of the cleaning solution is preferably about 37° C.±3°, or at the acceptable or preferred temperature of the user.

The method of using the vagina cleaning system is as follows. The first step is to prepare the cleaning solution and to add the solution to sprayer bottle. If the user prefers to use the functional cleaning solutions described above, one may either make those solutions or obtain them commercially. The second step is to lubricate the vagina opener and insert it into the vagina. The third step is to use the cleaning solution to remove unwanted materials from the vagina. When the user believes her vagina has been cleaned at the first inserted position of the vagina opener, she may change the vagina opener to another position to clean the rest of the previously unreached area. The washing process may take several minutes. The last step is to add health-promoting bacteria into the vagina by using the health-promoting bacteria introducer.

Cleaning the vagina may be done regularly regardless of sexual activity. One aim of the cleaning is to remove or reduce the concentration of the vaginal secretions, waste metabolites, and microorganisms. If it is to prevent pregnancy, the cleaning process should be started as soon as possible after semen has been ejaculated into the vaginal cavity. Because it is difficult to determine if a sexual partner carries pathogens of sexually transmitted diseases, it is always best to be safe and to clean the vagina after intercourse. In rape cases, the vagina cleaning system should be used as soon as possible to remove any potential pathogens the rapist might have deposited and to prevent the victim's unwanted pregnancy.

EXAMPLES

The following examples illustrate preferred uses of the present invention and are not limiting of the claims and specification in any way.

Example 1

Cleaning the Vagina on a Regular Basis

The subject was a middle aged female with a good health. After reading the instructions about the vagina cleaning procedure, she went to bathtub and filled the vagina-cleaning device with warm water. After lubricating the vagina opener with a bacitracin ointment, she gradually inserted the vagina opener to her vagina. Then, the warm water was sprayed into the vagina. At the beginning of the cleaning, she observed that the washout liquid was not clear. She slowly moved the vagina opener to a different position to let the warm water spray all parts of the vaginal cavity. After the two-minute wash, the washout liquid became clear. She changed the vagina opener to another different position and continued the cleaning process for another minute. When she found the outflow liquid clear, she stopped the cleaning process. After cleaning, the subject had a comfortable feeling about her vagina.

Example 2

Semen Removal from the Vagina

The subjects were a married couple. After they had intercourse, the female subject went to bathtub and connected the tube-like vagina-cleaning device with warm water. After she lubricated the vagina opener, she inserted the vagina opener. Before washing, she took a saline wetted cotton swab to get the first specimen from her vagina. At the beginning of the washing, she saw that the washout liquid seemed cloudy, like diluted milk. She continually sprayed all parts of the vaginal cavity with warm water. After washing for one minute, she found that the washout liquid became clear. She continued the cleaning process for another minute after she changed the vagina opener to another position. She took three saline-wetted swabs through the vagina opener from different parts of vagina to get the second set of the specimens. She gave both sets of specimens to the examiner. The examiner examined the glass slides under a light microscope. There were an un-countable number of sperm on the first swab, but no sperm were found on the second set of swabs.

Example 3
Fungi Removal from the Vagina

A married couple volunteered to participate in the experiment. Before starting the experiment, the female subject completed her regular vagina cleaning process. She used a cotton swab to collect a sample from her vagina. At the beginning of the experiment, the husband and wife made a yeast solution by mixing a half-teaspoon of baking yeast with one teaspoon of an evaporated milk, then adding that mixture to a glass cup containing ½ cup of pre-warmed saline. After well mixed, ¼ teaspoon of the mixture was injected into the vagina through the vagina opener. The female subject used a swab to collect the second sample from her vagina. After that, she started to clean her vagina by using the vagina cleaning solution containing a detergent. After a 2-minute wash, she collected three samples from her vagina at different positions. The examiner examined all samples under a light microscope. It was found that: (1) no yeast particles were found on the sample collected after the first vagina cleaning; (2) un-countable yeast particles were found from the sample collected after applying the yeast mixture to the vagina; (3) no yeast particles were found on the three samples collected after the second vagina cleaning using a soap solution.

Example 4
Removal of Bacteria from the Vagina

An adult female volunteered to participate in the experiment. Before starting the experiment, she completed her regular vagina cleaning process. Then, by using a regular cotton swab, she collected a sample from her vagina. At the beginning of the experiment, she took a swab and put it into yogurt. Then, she smeared her vagina with the swab adhered with yogurt. Then, she used a new swab to get a sample from her vagina for bacterial examination. After that, she started to clean her vagina by using vagina cleaning device and a vagina washing solution containing an antibiotic. After a 3-minute wash, she collected three samples from her vagina at different positions. The examiner examined all samples under a light microscope after Gram-staining. It was found that: (1) no bacteria were found on the sample collected after the regular vagina cleaning; (2) un-countable number of bacteria were found from the sample collected immediately after applying yogurt to the vagina; (3) no bacteria were seen on all three samples collected after the 3-minute vagina cleaning by using the antibiotic vagina cleaning solution.

Those skilled in the art will appreciate that changes and modifications can be made to the devices and method disclosed herein without departing from the spirit and scope of the present invention as set forth in the appended claims.

We claim:

1. A modular vaginal cleaning kit, comprising:
   a) a vaginal opener, wherein said vagina opener is an open-close tool with at least three legs connected to an open-close regulator;
   b) a single compressible spray bottle having a unidirectional air-flow switch and a uni-directional liquid-flow switch connected to a vaginal cleaning solution spray head;
   c) a vaginal cleaning solution for dispensing by said compressible spray bottle;
   d) said vaginal cleaning solution spray head adapted for releasable connection to said compressible spray bottle;
   e) a health-promoting bacteria; and
   f) a health-promoting bacteria dispensing nozzle adapted for releasable connection to said compressible spray bottle;
   wherein each of said vaginal cleaning solution and said health-promoting bacteria can be properly introduced to said vagina using said single spray bottle.

2. The vagina cleaning kit of claim 1 wherein said vaginal cleaning solution is a water-based buffer containing anti-microbial agents.

3. The vagina cleaning kit of claim 1 wherein said vaginal cleaning solution is a water-based buffer containing anti-inflammation agents.

4. The vagina cleaning kit of claim 1 wherein said vaginal cleaning solution is a water-based buffer containing detergents suitable for vaginal use.

5. The vagina cleaning kit of claim 1 wherein said vaginal cleaning solution is a water-based buffer containing spermicides.

6. A method of accomplishing vagina cleaning comprising:
   a) placing a vagina cleaning solution into a compressible spray bottle, said spray bottle adapted for releasable connection to one or more interchangeable dispensing nozzles;
   b) connecting a vagina cleaning solution dispensing nozzle to said compressible spray bottle;
   c) inserting a vagina opener into said vagina and operating said vagina opener to maintain said vagina in a dilated condition;
   d) inserting said vagina cleaning solution dispensing nozzle at least partially into said vagina;
   e) compressing said compressible spray bottle to dispense said vagina cleaning solution into said vagina;
   f) removing said vagina cleaning solution dispensing nozzle from said compressible spray bottle;
   g) connecting a health-promoting bacteria dispensing nozzle to said compressible spray bottle, said health-promoting bacteria dispenser pre-loaded with a health-promoting bacteria;
   h) inserting said health-promoting bacteria dispensing nozzle at least partially into said vagina;
   i) compressing said compressible spray bottle to dispense said health-promoting bacteria into said vagina; and
   j) removing said vagina opener from said vagina.

7. The method of claim 6 as used to remove unwanted material from the vaginal cavity.

8. The method of claim 7 wherein said unwanted material is semen.

9. The method of claim 7 wherein said unwanted material is sexually transmitted microorganisms.

10. The method of claim 7 wherein said unwanted material is waste metabolites.

11. The method of claim 6 as used to add health-promoting bacteria back into the vagina to prevent colonization of pathogenic microorganisms.

12. The method of claim 6 as used to add health-promoting bacteria back into the vagina to prevent abnormal colonization of microflora in the vagina.

13. The method of claim 6, wherein the steps of vagina cleaning are performed as in the order the steps are written.

14. The method of claim 6, wherein said health-promoting bacteria dispensing nozzle is supplied to the user pre-loaded.

15. The method of claim 6, wherein said health-promoting bacteria dispensing nozzle is pre-loaded by the user.

16. The method of claim 6, wherein any residual vagina cleaning solution is removed from said compressible spray bottle prior to health-promoting bacteria dispensing nozzle is attached thereto.

17. The method of claim 6, wherein each of said dispensing nozzles is disposable.

18. The method of claim 6, wherein each of said dispensing nozzles is re-useable.

19. The method of claim 6, wherein said vagina cleaning solution, said compressible spray bottle, said vagina cleaning solution dispensing nozzle, said health-promoting bacteria and, said health-promoting bacteria dispensing nozzle is a together as a kit.

* * * * *